US009186358B2

(12) United States Patent
Jomard et al.

(10) Patent No.: US 9,186,358 B2
(45) Date of Patent: Nov. 17, 2015

(54) COMBINATION THERAPY FOR TREATING OR PREVENTING AN INFLAMMATORY SKIN DISORDER

(75) Inventors: André Jomard, Saint Vallier de Thiey (FR); Françoise Delamadeleine, Antibes (FR)

(73) Assignee: GALDERMA LABORATORIES, L.P., Fort Worth, TX (US)

( * ) Notice: Subject to any disclaimer, the term of this patent is extended or adjusted under 35 U.S.C. 154(b) by 0 days.

(21) Appl. No.: 13/510,302

(22) PCT Filed: Nov. 18, 2010

(86) PCT No.: PCT/EP2010/067749
§ 371 (c)(1),
(2), (4) Date: Jun. 25, 2012

(87) PCT Pub. No.: WO2011/061252
PCT Pub. Date: May 26, 2011

(65) Prior Publication Data
US 2013/0116259 A1 May 9, 2013

(30) Foreign Application Priority Data
Nov. 18, 2009 (EP) .................................... 09176392

(51) Int. Cl.
*A61K 31/498* (2006.01)
*A61K 31/196* (2006.01)
*A61K 45/06* (2006.01)
*A61K 9/00* (2006.01)
*A61K 9/06* (2006.01)

(52) U.S. Cl.
CPC ............. *A61K 31/498* (2013.01); *A61K 9/0014* (2013.01); *A61K 9/06* (2013.01); *A61K 31/196* (2013.01); *A61K 45/06* (2013.01)

(58) Field of Classification Search
USPC ........................................................ 514/249
See application file for complete search history.

(56) References Cited

U.S. PATENT DOCUMENTS

| 3,278,447 A | 10/1966 | McNicholas |
|---|---|---|
| 3,560,501 A | 2/1971 | Walker |
| 3,594,380 A | 7/1971 | Sulkowski |
| 3,723,432 A | 3/1973 | Ott |
| 3,736,297 A | 5/1973 | Bracke |
| 3,740,442 A | 6/1973 | Ott |
| 3,890,319 A | 6/1975 | Danielewicz et al. |
| 4,029,792 A | 6/1977 | Danielewicz et al. |
| 4,164,570 A | 8/1979 | Clough et al. |
| 4,201,211 A | 5/1980 | Chandrasekaran et al. |
| 4,256,763 A | 3/1981 | McHugh |
| 4,285,967 A | 8/1981 | Gubernick et al. |
| 5,021,416 A | 6/1991 | Gluchowski |
| 5,077,292 A | 12/1991 | Gluchowski |
| 5,112,822 A | 5/1992 | Gluchowski |
| 5,130,441 A | 7/1992 | Gluchowski |
| 5,198,442 A | 3/1993 | Gluchowski |
| 5,204,347 A | 4/1993 | Gluchowski |
| 5,237,072 A | 8/1993 | Gluchowski |
| 5,300,504 A | 4/1994 | Gluchowski |
| 5,326,763 A | 7/1994 | Gluchowski et al. |
| 5,373,010 A | 12/1994 | Gluchowski et al. |
| 5,418,234 A | 5/1995 | Gluchowski et al. |
| 5,424,078 A | 6/1995 | Dziabo et al. |
| 5,442,053 A | 8/1995 | della Valle et al. |
| 5,552,403 A | 9/1996 | Burke et al. |
| 5,561,132 A | 10/1996 | Burke et al. |
| 5,587,376 A | 12/1996 | Burke et al. |
| 5,693,646 A | 12/1997 | Jones et al. |
| 5,696,127 A | 12/1997 | Jones et al. |
| 5,703,077 A | 12/1997 | Burke et al. |
| 5,714,486 A | 2/1998 | Burke et al. |
| 5,720,962 A | 2/1998 | Ivy et al. |
| 5,721,237 A | 2/1998 | Myers et al. |
| 5,736,165 A | 4/1998 | Ripley et al. |
| 5,753,637 A | 5/1998 | Fried |
| 5,756,503 A | 5/1998 | Burke et al. |
| 5,773,440 A | 6/1998 | Burke et al. |
| 5,916,574 A | 6/1999 | Fried et al. |
| 6,117,871 A | 9/2000 | Maurer et al. |
| 6,117,877 A | 9/2000 | Fogel |
| 6,194,415 B1 | 2/2001 | Wheeler et al. |
| 6,248,741 B1 | 6/2001 | Wheeler et al. |
| 6,284,765 B1 | 9/2001 | Caffrey |
| 6,294,553 B1 | 9/2001 | Gil et al. |

(Continued)

FOREIGN PATENT DOCUMENTS

| CN | 101305982 A | 11/2008 |
|---|---|---|
| CN | 101588791 A | 11/2009 |

(Continued)

OTHER PUBLICATIONS

Office Action issued Feb. 16, 2012 in U.S. Appl. No. 12/621,942.
Int'l Search Report issued Sep. 16, 2011 in Int'l Application No. PCT/EP2010/067749; Written Opinion.
Dachir et al, "Potential anti-inflammatory treatments against cutaneous sulfur mustard injury using the mouse ear vesicant model", Human and Experimental Toxicology, vol. 21, No. 4, pp. 197-203 (2002).

(Continued)

*Primary Examiner* — Kathrien Cruz
(74) *Attorney, Agent, or Firm* — Panitch Schwarze Belisario & Nadel LLP

(57) ABSTRACT

Methods and compositions for improved treatment and prevention of an inflammatory skin disorder or a sign and/or symptom associated with the skin disorder are described. The methods involve topical application to the skin a combination of a therapeutically effective amount of an α2 adrenergic receptor agonist, such as brimonidine, and a therapeutically effective amount of a non-steroidal anti-inflammatory agent, such as diclofenac.

2 Claims, 2 Drawing Sheets

(56) References Cited

U.S. PATENT DOCUMENTS

| | | | |
|---|---|---|---|
| 6,323,204 | B1 | 11/2001 | Burke et al. |
| 6,387,383 | B1 | 5/2002 | Dow et al. |
| 6,432,934 | B1 | 8/2002 | Gilbard |
| 6,441,047 | B2 | 8/2002 | DeSantis, Jr. |
| 6,444,681 | B1 | 9/2002 | Flavahan et al. |
| 6,465,464 | B2 | 10/2002 | Wheeler et al. |
| 6,468,989 | B1 | 10/2002 | Chang et al. |
| 6,517,847 | B2 | 2/2003 | Dow et al. |
| 6,534,048 | B1 | 3/2003 | Borgman |
| 7,014,858 | B2 | 3/2006 | Ashley |
| 7,439,241 | B2 | 10/2008 | DeJovin et al. |
| 7,812,049 | B2 | 10/2010 | Shanler et al. |
| 7,838,563 | B2 | 11/2010 | DeJovin et al. |
| 8,252,838 | B2 | 8/2012 | Kisak et al. |
| 2002/0197300 | A1 | 12/2002 | Schultz et al. |
| 2003/0017199 | A1 | 1/2003 | Woodward et al. |
| 2003/0068343 | A1 | 4/2003 | Muizzuddin et al. |
| 2003/0077301 | A1 | 4/2003 | Maibach et al. |
| 2003/0087962 | A1 | 5/2003 | Demopulos et al. |
| 2003/0229088 | A1 | 12/2003 | Gil et al. |
| 2004/0092482 | A1 | 5/2004 | Gupta |
| 2004/0156873 | A1 | 8/2004 | Gupta |
| 2004/0220259 | A1 | 11/2004 | Yu et al. |
| 2004/0242588 | A1 | 12/2004 | Dejovin et al. |
| 2004/0254252 | A1 | 12/2004 | Engles et al. |
| 2004/0266776 | A1 | 12/2004 | Gil et al. |
| 2005/0020600 | A1 | 1/2005 | Scherer |
| 2005/0059664 | A1 | 3/2005 | Gil et al. |
| 2005/0059744 | A1 | 3/2005 | Donello et al. |
| 2005/0124593 | A1 | 6/2005 | Bernstein |
| 2005/0165079 | A1 | 7/2005 | Shanler et al. |
| 2005/0276830 | A1 | 12/2005 | DeJovin et al. |
| 2006/0062750 | A1* | 3/2006 | Nordsiek et al. ........... 424/70.13 |
| 2006/0264515 | A1 | 11/2006 | Dejovin et al. |
| 2007/0082070 | A1 | 4/2007 | Stookey et al. |
| 2007/0207222 | A1 | 9/2007 | Yu et al. |
| 2008/0044497 | A1 | 2/2008 | Sussan et al. |
| 2009/0061020 | A1 | 3/2009 | Theobald et al. |
| 2009/0312429 | A1 | 12/2009 | Safonova et al. |
| 2010/0021402 | A1 | 1/2010 | DeJovin et al. |

FOREIGN PATENT DOCUMENTS

| | | |
|---|---|---|
| EP | 0055029 A2 | 6/1982 |
| EP | 1090630 A1 | 4/2001 |
| EP | 2090307 A1 | 8/2009 |
| FR | 2909876 A1 | 6/2008 |
| GB | 1381979 A | 1/1975 |
| JP | H08-208487 A | 8/1996 |
| JP | H08-259465 A | 10/1996 |
| JP | H10-265365 A | 10/1998 |
| JP | 2007-246450 A | 9/2007 |
| WO | 9100088 A1 | 1/1991 |
| WO | 9310791 A1 | 6/1993 |
| WO | 9613267 A2 | 5/1996 |
| WO | 9625163 A1 | 8/1996 |
| WO | 9836730 A2 | 8/1998 |
| WO | 0076502 A1 | 12/2000 |
| WO | 0211683 A1 | 2/2002 |
| WO | 2004105703 A2 | 12/2004 |
| WO | 2005002580 A1 | 1/2005 |
| WO | 2005010025 A2 | 2/2005 |
| WO | 2005115395 A2 | 12/2005 |
| WO | 2007103555 A2 | 9/2007 |
| WO | 2009032223 A1 | 3/2009 |
| WO | 2009129147 A2 | 10/2009 |

OTHER PUBLICATIONS

Jarvis et al, "Topical 3% Diclofenac in 2.5% Hyaluronic Acid Gel—A Review of its Use in Patients with Actinic Keratoses", American Journal of Clinical Dermatology, vol. 4, No. 3, pp. 203-213 (2003).

Int'l Search Report issued on Mar. 29, 2011 in Int'l Application No. PCT/US2010/057184; Written Opinion.

Ramey et al, "Rhinitis Medicamentosa", J Investig Allergol Clin Immunol, vol. 16, No. 3, pp. 148-155 (2006).

McGhie, "Brinnonidine: An alpha-2 adrenergic agonist for glaucoma", Journal of the Pharmacy Society of Wisconsin, May/Jun. 2001, pp. 32-36.

Arndt et al, "Manual of Dermatologic Therapeutics", 7th Ed., pp. 176-177 (2007).

Cunliffe et al, Br. Med. J. 105 (1977).

Shanler et al, "Arch Dermatol", vol. 143, No. 11, pp. 1369-1371 (2007).

Wilkin et al, J. Am. Acad. Dermatol., vol. 46, pp. 584-587 (2002).

Webster, "Rosacea and related disorders", Dermatology, vol. 1, Chapter 39, pp. 545-552 (2003).

Wymenga et al, "Management of Hot Flushes in Breast Cancer Patients", Acta Ocologica, vol. 41, No. 3, pp. 269-275 (2002).

Scruggs, "The Teardrop Sign: a Rare Dermatological Reaction to Brimonidine", Br. J. Opthalmol., vol. 84, pp. 671-672 (2000).

Sakakibara et al, "Treatment of Primary Erythromelalgia with Cyproheptadine", Journal of the Autonomic Nervous System, vol. 58, Nos. 1-2, pp. 121-122 (1996).

Jeyara et al, "Cooling Evokes Redistribution of a2C-Andrenoceptors from Golgi to Plasma Membrance in Transfected Human Embryonic Kidney 293 Cells", Molecular Pharmacology, vol. 60, No. 6, pp. 1195-1200 (2001).

Fuchs et al, "Heat, but not Mechanical Hyperalgesia, following Andrenergic Injections in Normal Human Skin", Pain, vol. 90, Nos. 1-2, pp. 15-23 (2001).

Morrison et al, "Andrenergic Modulation of a Spinal Sympathetic Reflex in the Rat", J. Pharmacol. Experim. Therap., vol. 273, No. 1, pp. 380-385 (1995).

Yaksh et al, "Reversal of Nerve Ligation-Induced Allodynia by Spinal Alpha-2 Andrenoceptor Agonists", J. Pharmacol. Experim. Therap., vol. 272, No. 1, pp. 207-214 (1995).

Waldron et al, "Relative Contribution of Different Vascular Beds to the Pressor Effects of a-Adrenoceptor Agonists and Vasopressin in Pithed Rats: Radioactive Microsphere Determination", J. Auton. Pharmac., vol. 5, pp. 333-338 (1985).

Bockman et al, "Binding and Functional Characterization of Alpha-2 Andrenergic Receptor Subtypes on Pig Vascular Endothelium", J. Pharmacol. Exp. Therapeutics, vol. 267, pp. 1126-1133 (1993).

Burke et al, "Preclinical Evaluation of Brimonidine", Survey of Ophthalmology, vol. 41, pp. S9-S18 (1996).

Chein et al, "Corneal and conjunctival/scleral penetration of p-aminoclonidine, AGN 190342 and clonidine in rabbit eyes", Current Eye Research, vol. 9, No. 11 pp. 1051-1059 (1990).

Chotani et al, "Silent asc-adrenergic receptors enable cold-induced vasoconstriction in cutaneous arteries", Am. J. Physiol. Heart Circ. Physiol., vol. 278, pp. H1075-H1083 (2000).

Freedman et al, "Estrogen raises the sweating threshold in postmenopausal women with hot flashes", Fertility and Sterility, vol. 77, No. 3, pp. 487-490 (2002).

Guarrera et al, "Flushing in Rosacea: A Possible Mechanism", Arch. Dermatol. Res., vol. 272, pp. 311-316 (1982).

Nakamura et al, "Peripheral analgesic action of clonidine: mediation by release of endogenous enkephlin-like substances", European Journal of Pharmacology, vol. 146, pp. 223-228 (1988).

Nielsen et al, "Postjunctional a2-adrenoceptors mediate vasoconstriction in human subcutaneous resistance vessels", Br. J. Pharmacol., vol. 97, pp. 829-834 (1989).

Walters, "Development and Use of Brimonidine in Treating Acute and Chronic Elevations of Intraocular Pressure: A Review of Safety, Efficacy, Dose Response, and Dosing Studies", Survey of Ophthalmology, vol. 41, pp. S19-S26 (1996).

Wilkin, "Effect of Subdepressor Clonidine on Flushing Reactions in Rosacea", Arch. Dermatol., vol. 119, pp. 211-214 (1983).

Wilkin, "Why is flushing limited to a mostly facial cutaneous distribution?", J. Am. Acad. Dermatol., vol. 19, pp. 309-313 (1988).

Rebora, "The Management of Rosacea", Am. J. Clin. Dermatol., vol. 3, No. 7, pp. 489-496 (2002).

(56) References Cited

OTHER PUBLICATIONS

Lindgren et al, "Effects of Some Antihypertensive Drugs on Cutaneous Blood Flow and Inflammatory Skin Responses Following Allergen Challenge in Guinea Pigs", Pharmacology and Toxicology, vol. 60, pp. 364-367 (1987).
Material Safety Data Sheet, pp. 1-2 (1997).
Gennaro, "Remington: The Science and Practice of Pharmacy", 19th Ed., pp. 866-885, 1517-1518, 1577-1597, 1672-1673 (1995).
Berge et al, "Pharmaceutical Salts", Journal of Pharmaceutical Sciences, vol. 66, No. 1, pp. 1-19 (1977).
Culp et al., "Rosacea: A Review," Pharmacy & Therapeutics, vol. 34, No. 1, pp. 38-45 (2009).
Roberson et al., "Psoriasis genetics: breaking the barrier," Trends in Genetics, vol. 26, No. 9, pp. 415-423 (2010).
Kurian et al., "Current Effective Topical Therapies in the Management of Psoriasis," Skin Therapy Letter, vol. 16, No. 1, pp. 4-7 (2011).
Schön et al., "Psoriasis", The New England Journal of Medicine, vol. 352, No. 18, pp. 1899-1912 (2005).
Korting et al., "Liposome encapsulation improves efficacy of betamethasone dipropionate in atopic eczema but not in psoriasis vulgaris," European Journal of Clinical Pharmacology, vol. 39, pp. 349-351 (1990).
Khandpur et al., "Topical immunomodulators in dermatology," Journal of Postgraduate Medicine, vol. 50, No. 2, pp. 131-139 (2004).
Ruffolo et al., "Receptor Interactions of Imidazolines: alpha-Adrenoceptors of Rat and Rabbit Aortae Differentiated by Relative Potencies, Affinities and Efficacies of Imidazoline Agonists," British Journal of Pharmacology, vol. 77, pp. 169-176 (1982).
Waugh et al., "Phe-308 and Phe-312 in Transmembrane Domain 7 Are Major Sites of alpha1-Adrenergic Receptor Antagonist Binding," The Journal of Biological Chemistry, vol. 276, No. 27, pp. 25366-25371 (2001).
Pigini et al., "Structure-Activity Relationship at alpha-Adrenergic Receptors Within a Series of Imidazoline Analogues of Cirazoline," Bioorganic & Medicinal Chemistry, vol. 8, pp. 883-888 (2000).
Hieble et al., "Alpha- and Beta-Adrenoceptors: From the Gene to the Clininc. 1. Molecular Biology and Adrenoceptor Subclassification," Journal of Medicinal Chemistry, vol. 38, No. 18, pp. 3415-3444 (1995).
Szabo, "Imidazoline antihypertensive drugs: a critical review on their mechanism of action," Pharmacology & Therapeutics, vol. 93, pp. 1-35 (2002).
Balogh et al., "3D QSAR models for alpha2a-adrenoceptor agonists," Neurochemistry International, vol. 51, pp. 268-276 (2007).
Ruffolo et al., "Alpha- and Beta-Adrenoceptors: From the Gene to the Clink. 2. Structure-Activity Relationships and Therapeutic Applications," Journal of Medicinal Chemistry, vol. 38, No. 19, pp. 3681-3716 (1995).
Day et al., "Use of pimecrolimus cream in disorders other than atopic dermatitis," Journal of Cutaneous Medicine and Surgery, vol. 12, No. 1, pp. 17-26 (2008) (abstract only).
Kosari et al., "Case report: Fluocinonide-induced perioral dermatitis in a patient with psoriasis," Dermatology Online Journal, vol. 15, No. 3 (2009).
Duncan, "Differential inhibition of cutaneous T-cell-mediated reactions and epidermal cell proliferation by cyclosporin A, FK-506, and rapamycin," Journal of Investigative Dermatology, vol. 102, No. 1, pp. 84-88 (1994).
Nichols et al., "Structure-Activity Relationships for alpha-Adrenoceptor Agonists and Antagonists," Alpha-Adrenoceptors: Molecular Biology, Biochemistry and Pharmacology, ed: Robert R. Ruffolo, Jr., pub: Karger, pp. 75-114 (1991).
Int'l Preliminary Report on Patentability issued May 31, 2012 in Int'l Application No. PCT/US2010/057184.

* cited by examiner

COMBINATION THERAPY FOR TREATING OR PREVENTING AN INFLAMMATORY SKIN DISORDER

CROSS-REFERENCE TO RELATED APPLICATION

This application is a Section 371 of International Application No. PCT/EP2010/067749, filed Nov. 18, 2010, which was published in the English language on May 26, 2011, under International Publication No. WO 2011/061252 A2, and the disclosure of which is incorporated herein by reference.

BACKGROUND OF THE INVENTION

Many inflammatory skin disorders often result in unsightly and painful rashes, acne, persistent red veins, and acne-like skin eruptions, such as macules, nodules, and pustules that may ooze or crust. For example, rosacea, generally involves the cheeks, nose, chin, and forehead and the typical age of onset is 30 to 60 years. See e.g., Zuber T. J., Rosacea: Beyond First Blush 32 H OSP. P RACT. 188-189 (1997); *THE MERCK MANUAL* 813-814 (Keryn A. G. Lane et al. eds. 17th ed. 2001). Many people with rosacea incorrectly assume that they suffer from adult acne, sun or windburn, or the normal effects of aging. The symptoms of rosacea include frequent blushing and frequent irritation of the facial skin and increasingly severe erythema (abnormal redness of the skin) and telangiectasia (visible red lines due to abnormal dilatation of capillary vessels and arterioles). Pimple-like eruptions, which may be solid (called papules or nodules) or puss filled (known as pustules), may develop. Such eruptions often look like acne, but whiteheads or blackheads (open and closed comedones, respectively) are not normally present. More severe symptoms of rosacea include that characterized by rhinophyma (thickened, lobulated overgrowth of the sebaceous glands and epithelial connective tissue of the nose). If left untreated, rosacea can progress to irreversible disfigurement. Rosacea symptoms are often aggravated by sun exposure, changes or extremes in temperature, wind, and consumption of certain foods, such as spicy foods, caffeine, and alcohol.

There is no known cure for many inflammatory skin disorders, including inflammatory dermatologic disorders of the face, such as rosacea. Current treatments, which are directed to control redness, inflammation, and skin eruptions, are of limited effectiveness in many patients and, generally, can be used only for a limited duration. Standard treatments include avoidance of triggers such as sun exposure, wind exposure, alcohol consumption, spicy foods, and irritating facial cleansers, lotions, and cosmetics. Antibiotics are the traditional first line of therapy. Long-term treatment (5 to 8 weeks or more) with oral antibiotics such as tetracycline, minocycline, doxycycline or clarithromycin may control skin eruptions. Alternative oral treatments include vitamin A medications, such as isoretinoin and antifungal medications. Unfortunately, such oral medications often cause side effects and many people have limited tolerance. Topical treatments, such as with topically applied metronidazole, isoretinoin, steroids, azelaic acid, rentinoic acid or retinaldehyde, or vitamin C preparations, are available but have limited effectiveness and cannot treat all symptoms. For example, isoretinoin has serious teratogenic side-effects and female patients of child bearing age must use effective birth control or avoid the therapy. Surgery, such as the laser elimination of blood vessels, is typically a last resort and may be prescribed if other treatments are ineffective. In patients with nose hyperplasia, surgical reduction may improve the patient's cosmetic appearance, but does not treat the disease itself. Mixed light pulse (photoderm) therapy has proved somewhat effective for symptoms associated with certain inflammatory skin orders, such as rosacea, in some patients.

Agonists of the $\alpha 2$ adrenoceptors have been used therapeutically for a number of conditions including hypertension, congestive heart failure, angina pectoris, spasticity, glaucoma, diarrhea, and for the suppression of opiate withdrawal symptoms (J. P. Heible and R. R. Ruffolo Therapeutic Applications of Agents Interacting with $\alpha$-Adrenoceptors, p. 180-206 in *Progress in Basic and Clinical Pharmacology* Vol. 8, P. Lomax and E. S. Vesell Ed., Karger, 1991). Adrenoreceptor agonists, such as clonidine, have been primarily used orally, though a patch formulation is known.

Systemic side effects have been associated with the use of agonists of the $\alpha 2$ adrenoceptors. The side effects include, for example, cardiopulmonary effects of $\beta$-blockers like timolol; dryness of mouth, flush, fever, tachycardia, urinary retention, convulsion and irritability with atropine; hypertension with phenylephine; increased salivation, nausea, vomiting, diarrhea, stomach cramps, bronchial secretions, brionchial constriction, asthma, bradycardia, paresthesia with miotics; hypotension with clonidine; and dry mouth, fatigue and drowsiness with apraclonidine and brimonidine. See Canadian Patent No. CA2326690.

Published US Patent Application US20050276830 discloses $\alpha 2$ adrenergic receptor agonists and their use for treating or preventing inflammatory skin disorders.

Non-steroidal anti-inflammatory agents (NSAIDs) have been used to reduce inflammation and as analgesics. However, NSAIDS are associated with a wide spectrum of undesirable side-effects. For example, use of NSAIDs can cause direct and indirect irritation of the gastrointestinal tract (GIT), resulting in a number of adverse drug reactions (ADRs), such as nausea, dyspepsia, gastric ulceration/bleeding, and diarrhea. Risk of ulceration increases with long duration and with higher doses of NSAIDs. NSAIDs are also associated with a relatively high incidence of renal ADRs, such as salt and fluid retention and hypertension, and in rare instances, more severe renal conditions, such as interstitial nephritis, nephrotic syndrome, acute renal failure, and acute tubular necrosis. A meta-analysis of trials comparing NSAIDs found that, with the exception of naproxen, both the selective Cox-2 inhibitor and the traditional NSAID are associated with an increased cardiovascular risk (Kearney et al, *BMJ* 332:1302-1308 (2006)).

Accordingly, there remains a need of novel methods and compositions for ameliorating inflammatory skin disorders, such as rosacea, and their symptoms, with no or very little side effect. Such methods and compositions are described in the present application.

BRIEF SUMMARY OF THE INVENTION

It is now discovered that a combination of an $\alpha 2$ adrenergic receptor agonist and a non-steroidal anti-inflammatory agent, resulted in a major improvement in the treatment of inflammatory skin disorders, with no or little side effects.

In one general aspect, embodiments of the present invention relate to a method of treating or preventing an inflammatory skin disorder or a sign and/or symptom associated therewith in a subject. The method comprises topically administering to a skin area of the subject a topical composition comprising a therapeutically effective amount of an $\alpha 2$ adrenergic receptor agonist, a therapeutically effective amount of a non-steroidal anti-inflammatory agent, and a pharmaceutically acceptable carrier, wherein the skin area is, or is prone to be, affected by the inflammatory skin disorder or the symptom associated therewith.

In another general aspect, embodiments of the present invention relate to a topically administrable composition for treating or preventing an inflammatory skin disorder or a sign and/or symptom associated therewith in a subject. The composition comprises a therapeutically effective amount of an α2 adrenergic receptor agonist, a therapeutically effective amount of a non-steroidal anti-inflammatory agent, and a pharmaceutically acceptable carrier.

In yet another general aspect, embodiments of the present invention relate to a kit for treating or preventing an inflammatory skin disorder or a sign and/or symptom associated therewith in a subject. The kit comprises:

(1) a first topically administrable composition comprising a therapeutically effective amount of an $\alpha_2$ adrenergic receptor agonist and a pharmaceutically acceptable carrier;

(2) a second topically administrable composition comprising a therapeutically effective amount of a non-steroidal anti-inflammatory agent and a pharmaceutically acceptable carrier; and (3) instructions for topically administering the first topically administrable composition and the second topically administrable composition to a skin area of a subject, wherein the skin area is, or is prone to be, affected by the inflammatory skin disorder or the signs and/or symptoms associated therewith.

Other aspects, features and advantages of the invention will be apparent from the following disclosure, including the detailed description of the invention and its preferred embodiments and the appended claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments of the invention. It should be understood, however, that the invention is not limited to the precise arrangements and instrumentalities shown.

In the drawing.

DETAILED DESCRIPTION OF THE INVENTION

Figure 1:
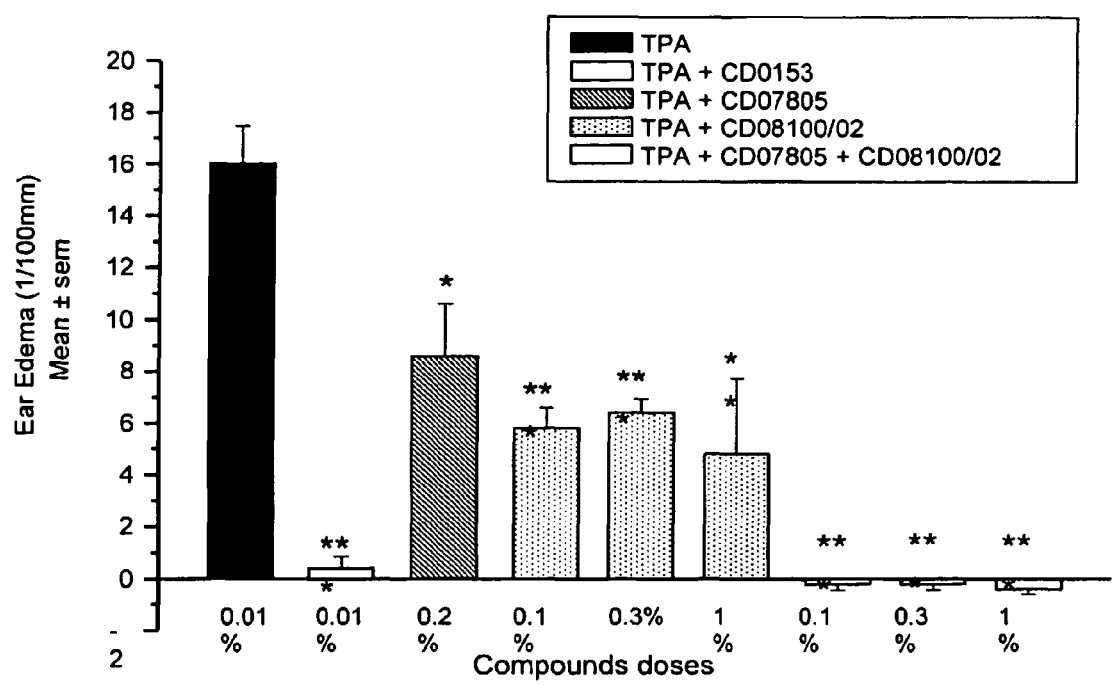
FIG. 1 illustrates the effect of brimonidine and diclofenac, alone or in combination, in reducing the TPA-induced ear edema in mice: the thickness of the ear was measured 6 hours after the topical administration of the compounds to the ear; the y axis represents the mean ear thickness measured from each group of 5 mice, and the x axis represents the concentration of the compounds.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

As used herein, the term "inflammatory skin disorder or a sign and/or symptom associated therewith" and "an inflammatory dermatologic disorder" mean any disease or medical condition associated with the skin, nails, or mucosal membranes displaying signs and/or symptoms of redness, flushing, burning, scaling, acne (pimples, papules, pustules (particularly in the absence of whiteheads and blackheads)), telangiectasis, sores, surface irritation or pain, itching, and/or inflammation. The degree or the severity of the disease or medical condition may vary. Exemplary inflammatory skin disorders or signs and/or symptoms associated therewith include, but are not limited to, dermatitis, such as contact dermatitis, atopic dermatitis, seborrheic dermatitis, nummular dermatitis, generalized exfoliative dermatitis, statis dermatitis, lichen simplex chronicus; disorders of hair follicles and sebaceous glands, such as acne, rosacea and rhinophyma, perioral dermatitis, and pseudofolliculitis barbae; and inflammatory reactions, such as drug eruptions, erythema multiforme, erythema nodosum, and granuloma annulare. In a preferred embodiment, the topical formulations of the invention are used to treat or prevent inflammatory dermatologic disorders of the face, such as rosacea.

There are four subtypes of rosacea: subtype I: erythematotelangiectactic rosacea (ETR): subtype II: papulopustular rosacea (PPR); subtype III: phymatous rosacea (PR); and subtype IV: ocular rosacea. Each subtype is then graded according to disease severity. See Wilkin J et al, 2004, *J Am Acad Dermatol.* 2004 June; 50(6):907-12; and Wilkin J et al, 2002, *J Am Acad Dermatol.* 2002 April; 46(4):584-7). This classification and grading system, based on clinical diagnosis, has helped to clarify the various components of rosacea and assisted clinicians in selecting therapy. But it is not known whether the different subtypes of rosacea represent different successive steps in the evolution of the disease or represent different diseases. The term "inflammatory skin disorder or a sign and/or symptom associated therewith" is intended to encompass all four subtypes of rosacea.

As used herein, an "α2 adrenergic receptor agonist" or "agonist of α2 adrenoceptor" means a compound that binds to and selectively stimulates alpha adrenergic receptor subclass $\alpha_2$. Such compounds can have powerful vasoconstricting effects when introduced into the body of mammals, particularly humans.

As used herein, the term "non-steroidal anti-inflammatory agent" or "NSAID" refers to a non-steroidal anti-inflammatory compound that inhibits the production of prostaglandins (PGs), which act (among other things) as messenger molecules in the process of inflammation. Most NSAIDs act as non-selective inhibitors of the enzyme cyclooxygenase (COX), including COX-1, COX-2, and possibly other COX isoenzymes. COX catalyzes the formation of PGs and thromboxane, primarily from arachidonic acid.

As used herein, the term "alkyl" means a saturated, monovalent, unbranched or branched hydrocarbon chain. Examples of alkyl groups include, but are not limited to, (C1-C3) alkyl groups, such as methyl, ethyl, propyl, isopropyl, and (C4-C8) alkyl groups, such as 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl-2,2-dimethyl-1-butyl, 3,3-dimethyl-1-butyl, 2-ethyl-1-butyl, butyl, isobutyl, sec-butyl, t-butyl, pentyl, isopentyl, neopentyl, hexyl, heptyl, octyl, and the like. An alkyl group can be unsubstituted or substituted with one or more suitable substituents.

As used herein, the term "alkoxy" means an oxygen ether radical of an alkyl. Examples of alkoxy include, but are not limited to, methoxy, ethoxy, n-propoxy, sec-butoxy, t-butoxy, n-hexyloxy and the like. An alkoxy group can be unsubstituted or substituted with one or more suitable substituents.

When a particular group is "substituted" (e.g., alkyl, alkoxy), that group can have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the term "halogen" means fluorine, chlorine, bromine, or iodine. Correspondingly, the term "halo" means fluoro, chloro, bromo, and iodo.

As used herein, the name of a compound is intended to encompass all possible existing isomeric forms (e.g., optical isomer, enantiomer, diastereomer, racemate or racemic mixture), esters, prodrugs, metabolite forms, or pharmaceutically acceptable salts, of the compound. For example, "brimonidine" can be the compound (5-bromo-quinoxalin-6-yl)-(4,5-dihydro-1H-imidazol-2-yl)-amine, and any pharmaceutically acceptable salt of the compound, such as brimonidine tartrate; "diclofenac" can be the compound 2-[2-(2,6-dichlorophenylamino)phenyl]acetic acid, and any pharmaceutically acceptable salt of the compound, such as the sodium or potassium salt of diclofenac.

The phrase "pharmaceutically acceptable salt(s)", as used herein, means those salts of a compound of interest that are safe and effective for topical use in mammals and that possess the desired biological activity. Pharmaceutically acceptable salts include salts of acidic or basic groups present in the specified compounds. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds used in the present invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 *J. PHARM. SCI.* 1-19 (1977), incorporated herein by reference.

As used herein, the term "hydrate" means a compound of interest, or a pharmaceutically acceptable salt thereof that further includes a stoichiometric or non-stoichiometric amount of water bound to it by non-covalent intermolecular forces.

The term "topically administrable composition," a "topical composition," or a "topical formulation," as used herein, means any formulation or composition which is pharmaceutically and/or cosmetically acceptable for topical delivery of the specified compounds according to the invention. Exemplary forms of formulation that can be used for topical administration include, but are not limited to, sprays, mists, aerosols, solutions, lotions, gels, creams, ointments, pastes, unguents, emulsions, and suspensions. The choice of topically administrable composition will depend on several factors, including the nature of the symptoms to be treated or prevented, the physiochemical characteristics of the particular compound to be administered and of other excipients present, their stability in the formulation, available manufacturing equipment, and cost constraints.

As used herein, the term "composition" is intended to encompass a product comprising the specified ingredients in the specified amounts, as well as any product which results, directly or indirectly, from combinations of the specified ingredients in the specified amounts.

As used herein, "carbomer" is the USP designation for various polymeric acids that are dispersible but insoluble in water. When the acid dispersion is neutralized with a base a clear, stable gel is formed. Carbomer 934P is physiologically inert and is not a primary irritant or sensitizer. Other carbomers include 910, 940, 941, and 1342.

As used herein, the term "subject" means any animal, preferably a mammal, most preferably a human, to whom will be or has been administered compounds or topical formulations according to embodiments of the invention. The term "mammal" as used herein, encompasses any mammal. Examples of mammals include, but are not limited to, cows, horses, sheep, pigs, cats, dogs, mice, rats, rabbits, guinea pigs, monkeys, humans etc., more preferably, a human. Preferably, a subject is in need of, or has been the object of observation or experiment of treatment or prevention of an inflammatory skin disorder and symptoms associated therewith.

As used herein, the term "instructions" when used in the context of a kit includes a publication, a recording, a diagram or any other medium of expression which can be used to communicate the usefulness of the kit for its designated use. The instructions can, for example, be affixed to or included within a container for the kit.

In one embodiment, "treatment" or "treating" refers to an amelioration, prophylaxis, or reversal of a disease or disorder, or at least one discernible symptom thereof, for example, treating an inflammatory skin disorder (e.g., rosacea) by lessening the redness of the skin. In another embodiment, "treatment" or "treating" refers to an amelioration, prophylaxis, or reversal of at least one measurable physical parameter related to the disease or disorder being treated, not necessarily discernible in or by the mammal. In yet another embodiment, "treatment" or "treating" refers to inhibiting or slowing the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

In certain embodiments, compounds of interest are administered as a preventative measure. As used herein, "prevention" or "preventing" refers to a reduction of the risk of acquiring a given disease or disorder. In a preferred mode of the embodiment, the specified compounds are administered as a preventative measure to a subject having a predisposition to a inflammatory skin disorder, such as rosacea, even though symptoms of the disorder are absent or minimal.

As used herein, a "therapeutically effective amount of an α2 adrenergic receptor agonist" means the amount of the α2 adrenergic receptor agonist that elicits the biological or medicinal response in a tissue system, animal or human that is being sought by a researcher, veterinarian, medical doctor or other clinician, which includes alleviation of the symptoms of the disease or disorder being treated. In a preferred embodiment, the therapeutically effective amount of an α2 adrenergic receptor agonist is effective to treat, improve the treatment of, or prophylactically prevent an inflammatory skin disorder or a sign and/or symptom associated therewith.

As used herein, a "therapeutically effective amount of a non-steroidal anti-inflammatory agent" means the amount of the non-steroidal anti-inflammatory agent that elicits the biological or medicinal response in a tissue system, animal or human that is being sought by a researcher, veterinarian, medical doctor or other clinician, which includes alleviation of the symptoms of the disease or disorder being treated. In a preferred embodiment, the therapeutically effective amount of non-steroidal anti-inflammatory agent is effective to treat, improve the treatment of, or prophylactically prevent an inflammatory skin disorder or a sign and/or symptom associated therewith.

In one general aspect, the present invention relates to a method of treating or preventing an inflammatory skin disorder or a sign and/or symptom associated therewith in a subject. The method comprises topically administering to a skin area of the subject a composition comprising a pharmaceutically acceptable carrier, a therapeutically effective amount of an α2 adrenergic receptor agonist and a therapeutically effective amount of a non-steroidal anti-inflammatory agent, wherein the skin area is, or is prone to be, affected by the inflammatory skin disorder or the symptom associated therewith.

Other aspects of the present invention include compositions, e.g., topically administrable compositions, and kits that can be used for treating or preventing an inflammatory skin disorder or a sign and/or symptom associated therewith in a subject. The composition or kit according to embodiments of the invention comprises a therapeutically effective amount of an α2 adrenergic receptor agonist and a therapeutically effective amount of a non-steroidal anti-inflammatory agent.

Methods and compositions according to the present invention can be used to treat or prevent any inflammatory skin disorder or a sign and/or symptom associated therewith, examples of which include, but are not limited to, conditions associated with cell proliferation, such as psoriasis, eczema and dermatitis, (e.g., eczematous dermatitides, topic, atopic or seborrheic dermatitis, allergic or irritant contact dermatitis, nummular dermatitis, generalized exfoliative dermatitis, eczema craquelee, photoallergic dermatitis, phototoxic dermatitis, phytophotodermatitis, radiation dermatitis, and stasis dermatitis, lichen simplex chronicus); scleroderma, ulcers and erosions resulting from trauma, burns, bullous disorders or ischemia of the skin or mucous membranes; several forms of ichthyoses, epidermolysis bullosae, hypertrophic scars, keloids; cutaneous changes of intrinsic aging, photoaging; frictional blistering caused by mechanical shearing of the skin and cutaneous atrophy resulting from the topical use of corticosteroids, inflammation of mucous membranes, such as cheilitis, chapped lips, nasal irritation, mucositis and vulvovaginitis.

Examples of inflammatory skin disorder or a sign and/or symptom associated therewith that can be treated or prevented by methods according to embodiments of the present invention also include, but are not limited to, disorders of hair follicles and sebaceous glands, such as acne, rosacea and rhinophyma, perioral dermatitis, and pseudofolliculitis barbae; and inflammatory reactions, such as drug eruptions, erythema multiforme, erythema nodosum, and granuloma annulare.

In a preferred embodiment, the method according to embodiments of the invention is used to treat or prevent inflammatory dermatologic disorders of the face, such as rosacea or a sign and/or symptom associated with rosacea, e.g., erythema of rosacea. Other preferred examples of inflammatory skin disorders that can be treated or prevented by methods according to embodiments of the invention include, but are not limited to, psoriasis, topic dermatitis, and acne.

In an embodiment of the present invention, the α2 adrenergic receptor agonists include, but are not limited to, the α2 adrenergic receptor agonists disclosed in the published US Patent Application US20050276830, which is herein incorporated by reference in its entirety.

In one embodiment of the present invention, the α2 adrenergic receptor agonist is a compound of formula (I):

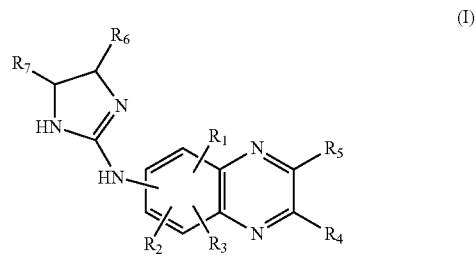

(I)

wherein each of $R_1$, $R_2$, and $R_3$ is independently hydrogen, hologen, alkyl, preferably unsubstituted alkyl, or alkoxy, preferably unsubstituted alkoxy; each of $R_4$ and $R_5$ is independently hydrogen, alkyl, preferably unsubstituted alkyl, or alkoxy, preferably unsubstituted alkoxy; and each of $R_6$ and $R_7$ is independently hydrogen, nitro, alkyl, preferably unsubstituted alkyl, or alkoxy, preferably unsubstituted alkoxy.

In a preferred embodiment, $R_6$ and $R_7$ are both hydrogen in formula (I).

In another preferred embodiment, $R_4$ and $R_5$ are both hydrogen in formula (I).

In one embodiment of the present invention, the α2 adrenergic receptor agonist is a compound of formula (Ia):

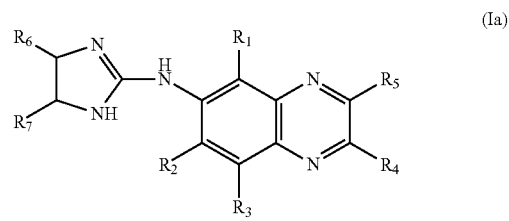

(Ia)

wherein each of $R_1$, $R_2$, and $R_3$ is independently hydrogen, hologen, alkyl, preferably unsubstituted alkyl, or alkoxy, preferably unsubstituted alkoxy; each of $R_4$ and $R_5$ is independently hydrogen, alkyl, preferably unsubstituted alkyl, or alkoxy, preferably unsubstituted alkoxy; and each of $R_6$ and $R_7$ is independently hydrogen, nitro, alkyl, preferably unsubstituted alkyl, or alkoxy, preferably unsubstituted alkoxy.

In a preferred embodiment, $R_6$ and $R_7$ are both hydrogen in formula (Ia).

In another preferred embodiment, $R_4$ and $R_5$ are both hydrogen in formula (Ia).

In still another preferred embodiment, $R_2$ and $R_3$ are both hydrogen and $R_1$ is halo, preferably, bromo, in formula (Ia).

In one embodiment of the present invention, the α2 adrenergic receptor agonist is a compound of formula (Ib):

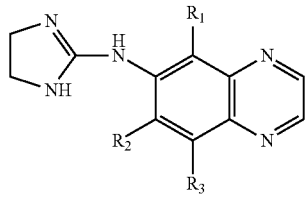

(Ib)

wherein each of $R_1$, $R_2$, and $R_3$ is independently hydrogen, halogen, alkyl, preferably, unsubstituted alkyl, or alkoxy, preferably, unsubstituted alkoxy.

In a preferred embodiment, $R_2$ and $R_3$ are both hydrogen and $R_1$ is halo, preferably, bromo, in formula (Ib)

In one embodiment of the present invention, the α2 adrenergic receptor agonist is a compound of formula (Ic):

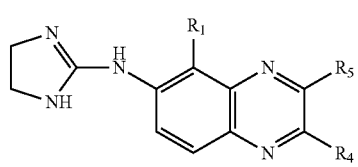

(Ic)

wherein $R_1$ is hydrogen, halogen, alkyl, preferably, unsubstituted alkyl, or alkoxy, preferably unsubstituted alkoxy.

In a preferred embodiment, $R_1$ is halo, more preferably, bromo; and each of $R_4$ and $R_5$ is independently hydrogen, alkyl, preferably, unsubstituted alkyl, or alkoxy, preferably, unsubstituted alkoxy, in formula (Ic).

In a preferred embodiment, at least one of $R_4$ and $R_5$ is hydrogen in formula (Ic).

In one embodiment of the present invention, the α2 adrenergic receptor agonist is a compound of formula (Id):

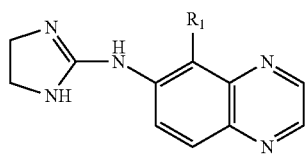

(Id)

wherein $R_1$ is hydrogen, halogen, alkyl, preferably, unsubstituted alkyl, or alkoxy, preferably, unsubstituted alkoxy.

In a preferred embodiment, $R_1$ is halo, more preferably, bromo, in formula (Id).

In another embodiment of the present invention, the α2 adrenergic receptor agonist is a compound of formula (II):

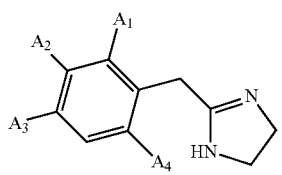

(II)

wherein each of $A_1$, $A_3$, and $A_4$ is independently hydrogen or alkyl; and $A_2$ is independently hydrogen or hydroxy.

In another embodiment of the present invention, the α2 adrenergic receptor agonist is a compound of formula (III):

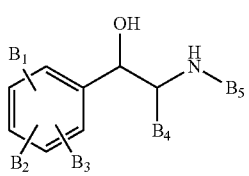

(III)

wherein each of $B_1$, $B_2$, and $B_3$ is independently hydrogen, hydroxy, or alkoxy, preferably methoxy; and each of $B_4$ and $B_5$ is independently hydrogen or alkyl.

Representative α2 adrenergic receptor agonists that can be used in the present invention include, but are not limited to, those listed in Table 1.

TABLE 1

Representative α2 adrenergic receptor agonists

| Compound Formula | Compound Name |
|---|---|
| | (5-Bromo-quinoxalin-6-yl)-(4,5-dihydro-1H-imidazol-2-yl)-amine (Brimonidine) |
| | (8-Bromo-quinoxalin-6-yl)-(4,5-dihydro-1H-imidazol-2-yl)-amine |
| | (8-Bromo-quinoxalin-5-yl)-(4,5-dihydro-1H-imidazol-2-yl)-amine |
| | (5-Bromo-3-methyl-quinoxalin-6-yl)-(4,5 dihydro-1H-imidazol-2-yl)-amine |

TABLE 1-continued

Representative α2 adrenergic receptor agonists

| Compound Formula | Compound Name |
|---|---|
| | (5-Bromo-2-methoxy-quinoxalin-6-yl)-(4,5-dihydro-1H-imidazol-2-yl)-amine |
| | (4,5-dihydro-1H-imidazol-2-yl)-(8-methyl-quinoxalin-6-yl)-amine |
| | (4,5-dihydro-1H-imidazol-2-yl)-quinoxalin-5-yl-amine |
| | Tetrahydrozaline |
| | Naphazoline |
| | Oxymetazoline |
| | Xylometazoline |
| | Epinephrine |
| | Norepinephrine |
| | Phenylephrine |
| | Methoxyamine |

The most preferred α2 adrenergic receptor agonist is brimonidine, (5-Bromo-quinoxalin-6-yl)-(4,5-dihydro-1H-imidazol-2-yl)-amine and pharmaceutically acceptable salts thereof, such as the tartrate salt of brimonidine.

Other examples of α2 adrenergic receptor agonists that can be used in the present invention include, but are not limited to, Dexmedetomidinc, Medetomidine, Romifidine, Clonidine, Detomidine, Lofexidine, Xylazine, Tizanidine, Guanfacine, and Amitraz.

In an embodiment of the present invention, the non-steroidal anti-inflammatory agent is selected from the group consisting of diclofenac, aspirin, ibuprofen, ketoprofen, piroxicam, naproxen, sulindac, choline subsalicylate, diflunisal, fenoprofen, indomethacin, meclofenamate, salsalate, tolmetin, and magnesium salicylate.

Preferably, the NSAID is diclofenac, 2-[2-(2,6-dichlorophenylamino)phenyl]acetic acid and pharmaceutically acceptable salts thereof, such as the sodium or potassium salt of diclofenac.

In a preferred embodiment, the method of the present invention comprises topically administering to the skin of a subject a composition comprising a therapeutically effective amount of brimonidine, a therapeutically effective amount of diclofenac, and a pharmaceutically acceptable carrier.

One skilled in the art will recognize that the therapeutically effective amount of the α2 adrenergic receptor agonist and the therapeutically effective amount of the NSAID to be used in the instant invention can vary with factors, such as the particular subject, e.g., age, diet, health, etc., severity and complications of the inflammatory skin disorder sought to be treated or prevented, the formulation used, etc. In view of the present disclosure, standard procedures can be performed to evaluate the effect of the administration of a topical composition to a subject, thus allowing a skilled artisan to determine the therapeutically effective amount of the α2 adrenergic receptor agonist and the therapeutically effective amount of the NSAID to be administered to the subject. For example, the clinically observable beneficial effect of the combination of the α2 adrenergic receptor agonist and NSAID in treating an inflammatory skin disorder or a sign and/or symptom associated therewith can be observed or monitored directly from the subject.

The clinically observable beneficial effect can be a situation that, when a composition of the present invention is administered to a subject after signs and/or symptoms related to an inflammatory skin disorder are observable, the signs and/or symptoms are prevented from further development or aggravation, or develop to a lesser degree than without administration of the specified composition according to embodiments of the present invention. The clinically observable beneficial effect can also be that, when a composition of the present invention is administered to a subject before signs and/or symptoms related to an inflammatory skin disorder are observable, the signs and/or symptoms are prevented from occurring or subsequently occur to a lesser degree than without administration of the composition of the present invention.

In one embodiment, a therapeutically effective amount of the α2 adrenergic receptor agonist in combination with a therapeutically effective amount of NSAID will reduce a syndrome or a condition of discomfort of the subject associated with the inflammatory skin disorder or a sign and/or symptom associated therewith by at least about 20%, for example, by at least about 30%, about 40%, about 50%, about 60%, about 70%, about 80%, about 90%, or about 100%.

In another embodiment, a therapeutically effective amount of the α2 adrenergic receptor agonist in combination with a therapeutically effective amount of NSAID will prevent a syndrome or a condition of discomfort of the subject associated with the inflammatory skin disorder or a sign and/or symptom associated therewith, or reduce the probability of its onset by at least about 20%, for example, by at least about 30%, about 40%, about 50%, about 60%, about 70%, about 80%, about 90%, or about 100%.

Methods of the present invention can be used in conjunction with one or more other treatments and medications for the inflammatory skin disorder or a sign and/or symptom associated therewith, such as those disclosed in THE MERCK MANUAL 811-830 (Keryn A. G. Lane et al. eds. 17th ed. 2001), hereby incorporated herein by reference.

The other medicament or treatment can be administered to the subject simultaneously with, or in a sequence and within a time interval of, the combined therapy of the α2 adrenergic receptor agonist and NSAID, such that the active ingredients or agents can act together to treat or prevent inflammatory skin disorders (e.g., rosacea) and signs and/or symptoms associated therewith. For example, the other medicament or treatment, the α2 adrenergic receptor agonist and the NSAID can be administered in the same or separate formulations at the same or different times.

Any suitable route of administration can be employed to deliver the additional treatment or medication including, but not limited to, oral, intraoral, rectal, parenteral, topical, epicutaneous, transdermal, subcutaneous, intramuscular, intranasal, sublingual, buccal, intradural, intraocular, intrarespiratory, or nasal inhalation.

In one embodiment, the topical formulations of the invention are used in combination with systemic administration of antibiotics or retinoids including, but not limited to, orally dosed antibiotics, such as tetracycline, minocin, minocycline, erythromycin, and doxycycline, and orally dosed retinoids such as isotretinoins (e.g., Accutane or Roaccutane).

In another embodiment, the topical formulations of the invention are used in combination with other topical treatments including, but not limited to, topical formulations consisting of metronidizole, hydrogen peroxide, benzoyl peroxide, lipoic acid, and azelaic acid, and sulfur preparations; topically dosed antibiotics, such as metronidazole, clindamycin, and erythromycin; topical retinoids such as tretinoin, adapalene, tazarotene; or topical steroids.

In another embodiment, the topical formulations of the invention are used in combination with mixed light pulse therapy (photoderm), pulsed dye laser treatment, or electrosurgery.

A topically administrable composition according to embodiments of the present invention comprises a pharmaceutically acceptable carrier, a therapeutically effective amount of an α2 adrenergic receptor agonist and a therapeutically effective amount of a non-steroidal anti-inflammatory agent. The carriers useful for topical delivery of the specified compounds according to embodiments of the invention can be any carrier known in the art for topically administering pharmaceuticals, including, but not limited to, pharmaceutically acceptable solvents, such as a polyalcohol or water; emulsions (either oil-in-water or water-in-oil emulsions), such as creams or lotions; micro emulsions; gels; ointments; liposomes; powders; and aqueous solutions or suspensions. The pharmaceutically acceptable carrier includes necessary and inert pharmaceutical excipients, including, but not limited to, binders, suspending agents, lubricants, flavorants, preservatives, dyes, and coatings.

The topically administrable composition according to embodiments of the present invention are prepared by mixing a pharmaceutically acceptable carrier with a therapeutically effective amount of an α2 adrenergic receptor agonist and a therapeutically effective amount of a non-steroidal anti-inflammatory agent according to known methods in the art, for example, methods provided by standard reference texts such as, REMINGTON: THE SCIENCE AND PRACTICE OF PHARMACY 1577-1591, 1672-1673, 866-885 (Alfonso R. Gennaro ed. 19th ed. 1995); Ghosh, T. K.; et al. TRANSDERMAL AND TOPICAL DRUG DELIVERY SYSTEMS (1997), both of which are hereby incorporated herein by reference.

In one embodiment, the topically administrable composition of the invention is in the form of an emulsion. Emulsions, such as creams and lotions are suitable topical formulations for use in the invention. An emulsion is a dispersed system comprising at least two immiscible phases, one phase dispersed in the other as droplets ranging in diameter from 0.1 µm to 100 µm. An emulsifying agent is typically included to improve stability. When water is the dispersed phase and an oil is the dispersion medium, the emulsion is termed a water-in-oil emulsion. When an oil is dispersed as droplets throughout the aqueous phase as droplets, the emulsion is termed an oil-in-water emulsion. Emulsions, such as creams and lotions that can be used as topical carriers and their preparation are disclosed in REMINGTON: THE SCIENCE AND PRACTICE OF PHARMACY 282-291 (Alfonso R. Gennaro ed. 19th ed. 1995), hereby incorporated herein by reference.

In another embodiment, the topically administrable composition of the invention is in the form of a gel, for example, a two-phase gel or a single-phase gel. Gels are semisolid systems consisting of suspensions of small inorganic particles or large organic molecules interpenetrated by a liquid. When the gel mass comprises a network of small discrete inorganic particles, it is classified as a two-phase gel. Single-phase gels consist of organic macromolecules distributed uniformly throughout a liquid such that no apparent boundaries exist between the dispersed macromolecules and the liquid. Suitable gels for use in the invention are disclosed in REMINGTON: THE SCIENCE AND PRACTICE OF PHARMACY 1517-1518 (Alfonso R. Gennaro ed. 19th ed. 1995), hereby incorporated herein by reference. Other suitable gels for use with the invention are disclosed in U.S. Pat. No.

6,387,383 (issued May 14, 2002); U.S. Pat. No. 6,517,847 (issued Feb. 11, 2003); and U.S. Pat. No. 6,468,989 (issued Oct. 22, 2002), each of which patents is hereby incorporated herein by reference.

In an embodiment, the topical composition further comprises an aqueous gel comprising water and a water-gelling amount of a pharmaceutically acceptable gelling agent selected from the group consisting of carbomers, glycerine polyacrylate, and mixtures thereof, and the topical composition has a physiologically acceptable pH.

Polymer thickeners (gelling agents) that may be used in compositions according to embodiments of the present invention include those known to one skilled in the art, such as hydrophilic and hydroalcoholic gelling agents frequently used in the cosmetic and pharmaceutical industries. Preferably, the hydrophilic or hydroalcoholic gelling agent comprises "CARBOPOL®" (B.F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), or "STABILEZE®" (ISP Technologies, Wayne, N.J.). Preferably the gelling agent comprises between about 0.2% to about 4% by weight of the composition. More particularly, the preferred compositional weight percent range for "CARBOPOL®" is between about 0.5% to about 2%, while the preferred weight percent range for "NATROLSOL®" and "KLUCEL®" is between about 0.5% to about 4%. The preferred compositional weight percent range for both "HYPAN®" and "STABILEZE®" is between 0.5% to about 4%.

"CARBOPOL®" is one of numerous cross-linked acrylic acid polymers that are given the general adopted name carbomer. These polymers dissolve in water and form a clear or slightly hazy gel upon neutralization with a caustic material such as sodium hydroxide, potassium hydroxide, triethanolamine, or other amine bases. "KLUCEL®" is a cellulose polymer that is dispersed in water and forms a uniform gel upon complete hydration. Other preferred gelling polymers include hydroxyethylcellulose, cellulose gum, MVE/MA decadiene crosspolymer, PVM/MA copolymer, or a combination thereof.

In another preferred embodiment, the topically administrable composition of the invention is in the form of an ointment. Ointments are oleaginous semisolids that contain little if any water. Preferably, the ointment is hydrocarbon based, such as a wax, petrolatum, or gelled mineral oil. Suitable ointments for use in the invention are well known in the art and are disclosed in REMINGTON: THE SCIENCE AND PRACTICE OF PHARMACY 1585-1591 (Alfonso R. Gennaro ed. 19th ed. 1995), hereby incorporated herein by reference.

In an embodiment of the present invention, the topically administrable composition of the invention comprises at least one of a cream and an ointment, each comprising an agent selected from the group consisting of stearic acid, stearyl alcohol, cetyl alcohol, glycerin, water, and mixtures thereof, and the topical composition has a physiologically acceptable pH.

In another embodiment, the topically administrable composition of the invention is in the form of an aqueous solution or suspension, preferably, an aqueous solution. Suitable aqueous topical formulations for use in the invention include those disclosed in REMINGTON: THE SCIENCE AND PRACTICE OF PHARMACY 1563-1576 (Alfonso R. Gennaro ed. 19th ed. 1995), hereby incorporated herein by reference. Other suitable aqueous topical carrier systems include those disclosed in U.S. Pat. No. 5,424,078 (issued Jun. 13, 1995); U.S. Pat. No. 5,736,165 (issued Apr. 7, 1998); U.S. Pat. No. 6,194,415 (issued Feb. 27, 2001); U.S. Pat. No. 6,248,741 (issued Jun. 19, 2001); U.S. Pat. No. 6,465,464 (issued Oct. 15, 2002), all of which patents are hereby incorporated herein by reference.

The pH of the topical formulations of the invention are preferably within a physiologically acceptable pH, e.g., within the range of about 6 to about 8, more preferably, of about 6.3 to about 6.5. To stabilize the pH, preferably, an effective amount of a buffer is included. In one embodiment, the buffering agent is present in the aqueous topical formulation in an amount of from about 0.05 to about 1 weight percent of the formulation. Acids or bases can be used to adjust the pH as needed.

Tonicity-adjusting agents can be included in the aqueous topical formulations of the invention. Examples of suitable tonicity-adjusting agents include, but are not limited to, sodium chloride, potassium chloride, mannitol, dextrose, glycerin, and propylene glycol. The amount of the tonicity agent can vary widely depending on the formulation's desired properties. In one embodiment, the tonicity-adjusting agent is present in the aqueous topical formulation in an amount of from about 0.5 to about 0.9 weight percent of the formulation.

Preferably, the aqueous topical formulations of the invention have a viscosity in the range of from about 15 cps to about 25 cps. The viscosity of aqueous solutions of the invention can be adjusted by adding viscosity adjusting agents, for example, but not limited to, polyvinyl alcohol, povidone, hydroxypropyl methyl cellulose, poloxamers, carboxymethyl cellulose, or hydroxyethyl cellulose.

In a preferred embodiment, the aqueous topical formulation of the invention is isotonic saline comprising a preservative, such as benzalkonium chloride or chlorine dioxide, a viscosity-adjusting agent, such as polyvinyl alcohol, and a buffer system such as sodium citrate and citric acid.

The topically administrable composition according to embodiments of the invention can comprise pharmaceutically acceptable excipients such as those listed in REMINGTON: THE SCIENCE AND PRACTICE OF PHARMACY 866-885 (Alfonso R. Gennaro ed. 19th ed. 1995; Ghosh, T. K.; et al. TRANSDERMAL AND TOPICAL DRUG DELIVERY SYSTEMS (1997), hereby incorporated herein by reference, including, but not limited to, protectives, adsorbents, demulcents, emollients, preservatives, antioxidants, moisturizers, buffering agents, solubilizing agents, skin-penetration agents, and surfactants.

Suitable protectives and adsorbents include, but are not limited to, dusting powders, zinc sterate, collodion, dimethicone, silicones, zinc carbonate, aloe vera gel and other aloe products, vitamin E oil, allatoin, glycerin, petrolatum, and zinc oxide.

Suitable demulcents include, but are not limited to, benzoin, hydroxypropyl cellulose, hydroxypropyl methylcellulose, and polyvinyl alcohol.

Suitable emollients include, but are not limited to, animal and vegetable fats and oils, myristyl alcohol, alum, and aluminum acetate.

In an embodiment, the topically administrable composition of the invention further comprises one or more agent selected from the group consisting of a preservative, a local anesthetic and a skin humectant.

Suitable preservatives include, but are not limited to, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other antimicrobial agents such as chlorhexidine, chlorocresol, benzoic acid and polymyxin.

Chlorine dioxide ($ClO_2$), preferably, stabilized chlorine dioxide, is a preferred preservative for use with topical formulations of the invention. The term "stabilized chlorine dioxide" is well known in the industry and by those skilled in the art. Stabilized chlorine dioxide includes one or more chlorine dioxide precursors such as one or more chlorine dioxide-containing complexes and/or one or more chlorite-containing components and/or one or more other entities capable of decomposing or being decomposed in an aqueous medium to form chlorine dioxide. U.S. Pat. No. 5,424,078 (issued Jun. 13, 1995), hereby incorporated herein by reference, discloses a form of stabilized chlorine dioxide and a method for producing same, which can be used as a preservative for aqueous ophthalmic solutions and is useful in topical formulations of the invention. The manufacture or production of certain stabilized chlorine dioxide products is described in U.S. Pat. No. 3,278,447, hereby incorporated herein by reference. A commercially available stabilized chlorine dioxide which can be utilized in the practice of the present invention is the proprietary stabilized chlorine dioxide of BioCide International, Inc. of Norman, Okla., sold under the trademark Purogene™ or Purite™. Other suitable stabilized chlorine dioxide products include that sold under the trademark DuraKlor by Rio Linda Chemical Company, Inc., and that sold under the trademark Antheium Dioxide by International Dioxide, Inc.

Suitable antioxidants include, but are not limited to, ascorbic acid and its esters, sodium bisulfite, butylated hydroxytoluene, butylated hydroxyanisole, tocopherols, and chelating agents like EDTA and citric acid.

Suitable moisturizers include, but are not limited to, glycerin, sorbitol, polyethylene glycols, urea, and propylene glycol.

Suitable buffering agents for use with the invention include, but are not limited to, acetate buffers, citrate buffers, phosphate buffers, lactic acid buffers, and borate buffers.

Suitable solubilizing agents include, but are not limited to, quaternary ammonium chlorides, cyclodextrins, benzyl benzoate, lecithin, and polysorbates.

Suitable skin-penetration agents include, but are not limited to, ethyl alcohol, isopropyl alcohol, octylphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate); and N-methylpyrrolidone.

The topically administrable composition according to embodiments of the invention can include pharmaceuticals or their pharmaceutically acceptable salts, such as an α2 adrenergic receptor agonist and a non-steroidal anti-inflammatory agent, and optionally one or more other pharmaceutically active ingredients, including, but not limited to, corticosteroids and other anti-inflammatory agents, such as betamethasone, diflorasone, amcinonide, fluocinolone, mometasone, hydrocortisone, prednisone, and triamcinolone; local anesthetics and analgesics, such as camphor, menthol, lidocaine, and dibucaine, and pramoxine; antifungals, such as ciclopirox, chloroxylenol, triacetin, sulconazole, nystatin, undecylenic acid, tolnaftate, miconizole, clotrimazole, oxiconazole, griseofulvin, econazole, ketoconazole, and amphotericin B; antibiotics and anti-infectives, such as mupirocin, erythromycin, clindamycin, gentamicin, polymyxin, bacitracin, and silver sulfadiazine; and antiseptics, such as iodine, povidine-iodine, benzalkonium chloride, benzoic acid, chlorhexidine, nitrofurazine, benzoyl peroxide, hydrogen peroxide, hexachlorophene, phenol, resorcinol, and cetylpyridinium chloride.

In a preferred embodiment, a topically administrable composition according to embodiments of the invention further comprises titanium dioxide ($TiO_2$), preferably at an amount that is sufficient to mask the color of brimonidine or another colored ingredient in the formulation, but would not cause irritation to the skin. $TiO_2$ may cause mild irritation and reddening to the eyes, thus eye contact with the $TiO_2$-containing topically administrable composition should be avoided.

Dosages and dosing frequency will be determined by a trained medical professional depending on the activity of the compounds used, the characteristics of the particular topical formulation, and the identity and severity of the dermatologic disorder treated or prevented.

In an embodiment of the present invention, the topically administrable composition comprises 0.01% to 5% by weight of the α2 adrenergic receptor agonist and 0.01% to 5% by weight of the non-steroidal anti-inflammatory agent. For example, the composition can comprise, 0.01%, 0.05%, 0.1%, 0.2%, 0.3%, 0.4%, 0.5%, 0.6%, 0.7%, 0.8%, 0.9%, 1%, 2%, 3%, 4% or 5%, by weight, of the α2 adrenergic receptor agonist; and 0.01%, 0.05%, 0.1%, 0.2%, 0.3%, 0.4%, 0.5%, 0.6%, 0.7%, 0.8%, 0.9%, 1%, 2%, 3%, 4% or 5% by weight, of the non-steroidal anti-inflammatory agent.

In a preferred embodiment, the topically administrable composition comprises 0.05-0.5%, 0.07%-0.7% or 0.1-0.6% by weight of the α2 adrenergic receptor agonist and 0.05%-0.5%, 0.1%-1%, or 0.5%-2% by weight of the non-steroidal anti-inflammatory agent.

To treat or prevent inflammatory skin disorders (e.g., rosacea), in view of the present disclosure, for example, the topically administrable compositions of the invention are topically applied directly to the affected area in any conventional manner well known in the art, e.g., by dropper or applicator stick, as a mist via an aerosol applicator, via an intradermal or transdermal patch, or by simply spreading a formulation of the invention onto the affected area with fingers. Generally the amount of a topical formulation of the invention applied to the affected skin area ranges from about 0.1 $g/cm^2$ of skin surface area to about 5 $g/cm^2$, preferably, 0.2 $g/cm^2$ to about 0.5 $g/cm^2$ of skin surface area. Typically, one to four applications per day are recommended during the term of treatment.

Another aspect of the invention relates to a kit that comprises one or more topical formulations according to embodiments of the invention in one or more suitable containers with labeling and instructions for use for treating or preventing an inflammatory skin disorder or a sign and/or symptom associated therewith. The kit comprises:

(1) a first topically administrable composition comprising a therapeutically effective amount of an $\alpha_2$ adrenergic receptor agonist and a pharmaceutically acceptable carrier;

(2) a second topically administrable composition comprising a therapeutically effective amount of a non-steroidal anti-inflammatory agent and a pharmaceutically acceptable carrier; and (3) instructions for topically administering the first topically administrable composition and the second topically administrable composition to a skin area of a subject, wherein the skin area is affected, or is prone to be affected, by the inflammatory skin disorder or the sign and/or symptom associated therewith.

In one embodiment of the invention, the first and the second topically administrable compositions are the same single topically administrable composition, which comprises both a therapeutically effective amount of an $\alpha_2$ adrenergic receptor agonist and a therapeutically effective amount of a non-steroidal anti-inflammatory agent. The single topically administrable composition is contained within one suitable container, such as a dropper, a jar, or a tube with a suitable small orifice size, such as an extended tip tube, made of any pharmaceutically suitable material.

In another embodiment, the first and the second topically administrable compositions are two separate individual topically administrable compositions, each comprising a therapeutically effective amount of an $\alpha_2$ adrenergic receptor agonist or a therapeutically effective amount of a non-steroidal anti-inflammatory agent, respectively. The two separate topically administrable compositions are contained within two suitable separate containers, such as a dropper, a jar, or a tube with a suitable small orifice size, such as an extended tip tube, made of any pharmaceutically suitable material.

The topical formulations of the invention can be filled and packaged into a plastic squeeze bottle or tube. Suitable container-closure systems for packaging a topical formulations of the invention are commercially available for example, from Wheaton Plastic Products, 1101 Wheaton Avenue, Millville, N.J. 08332.

Preferably, instructions are packaged with the formulations of the invention, for example, a pamphlet or package label. The labeling instructions explain how to administer topical formulations of the invention, in an amount and for a period of time sufficient to treat or prevent inflammatory skin disorders (e.g., rosacea) and signs and/or symptoms associated therewith, e.g., the instructions for topically administering the first topically administrable composition and the second topically administrable composition to the subject, either as one composition administered at the same time, or as two compositions administered at the same or different time points. Preferably, the label includes the dosage and administration instructions, the topical formulation's composition, the clinical pharmacology, drug resistance, pharmacokinetics, absorption, bioavailability, and contraindications.

This invention will be better understood by reference to the non-limiting examples that follow, but those skilled in the art will readily appreciate that the examples are only illustrative of the invention as described more fully in the claims which follow thereafter.

Example 1

Gel Formulation

An exemplary gel formulation is prepared using methods known in the art, e.g., by mixing the following ingredients at the specified concentrations:

| Ingredient | Weight Percentage |
|---|---|
| Brimonidine tartrate | 0.18% |
| Diclofenac sodium | 0.30% |
| Carbomer 934P | 1.25% |
| Methylparaben | 0.3% |
| Phenoxyethanol | 0.4% |
| Glycerin | 5.5% |
| 10% Titanium dioxide | 0.625% |
| Propylene glycol | 5.5% |
| 10% NaOH Solution | 6.5% |
| DI Water | QS |
| TOTAL | 100% |

Example 2

Improved Anti-Inflammatory Activity of the Combination of Brimonidine and Diclofenac in TPA-Induced Edema Animal Model The 12-O-tetradecanoylphorbol-13-acetate (TPA)-induced edema animal model was used to demonstrate the improved anti-inflammatory effect of brimonidine and diclofenac.

All procedures involving animals were conducted in a fully accredited animal facility and in accordance with preapproved protocols.

The edema inducer, TPA, was dissolved in ethanol at 0.01% by weight to obtain a TPA solution ("TPA solution"). Test compounds, brimonidine (CD07805) and diclofenac (CD08100/02), were dissolved in the TPA solution alone or in combination at desired concentrations. Positive control compound, betametasone valerate (CD0153), was dissolved in the TPA solution at 0.01% by weight.

Twenty (20) μl of each of the TPA solution (negative control), the test compound dissolved in the TPA solution, or the positive control dissolved in the TPA solution, was topically applied to an ear of the normal, 8-9 week old, female mice (BALB/c ByJ Rj). Different compounds at different dosages were tested on 10 groups of animals, each group having 5 mice (see Table 2).

TABLE 2

Groups of animals used in the TPA-induced edema experiment

| Groups: (compounds/dose) | Animal identification |
|---|---|
| Group 1: Ethanol | 1 to 5 |
| Group 2: TPA at 0.01% | 6 to 10 |
| Group 3: TPA + CD0153 at 0.01% | 11 to 15 |
| Group 4: TPA + CD07805 at 0.2% | 16 to 20 |
| Group 5: TPA + CD08100/02 at 0.1% | 21 to 25 |
| Group 6: TPA + CD08100/02 at 0.3% | 26 to 30 |
| Group 7: TPA + CD08100/02 at 1% | 31 to 35 |
| Group 8: TPA + CD07805 at 0.2% + CD08100/02 at 0.1% | 36 to 40 |
| Group 9: TPA + CD07805 at 0.2% + CD08100/02 at 0.3% | 41 to 45 |
| Group 10: TPA + CD07805 at 0.2% + CD08100/02 at 1% | 46 to 50 |

CD0153 is betametasone valerate, and TPA is 12-O-tetradecanoylphorbol-13-acetate.

The ear thickness of each of the 50 animals was measured at 6 hours after the compound application. After the measurement, the animals were sacrificed by carbon dioxide following a preapproved protocol.

The mean of the ear thickness measured from 5 animals in each of the 10 groups was calculated. The anti-inflammatory activity of a test compound was measured by its ability to reduce TPA-induced ear edema, i.e., as the percentage of reduction in ear thickness of animals treated with both the test compound and TPA as compared with that treated with TPA alone.

As shown in Table 3 and FIG. 1, after a single topical application, 0.2% brimonidine (CD07805) alone reduced TPA-induced ear edema in mice by 46.3%, demonstrating a moderate anti-inflammatory effect. Diclofenac (CD08100/02) alone at 0.1%, 0.3% and 1%, reduced TPA-induced ear edema in mice by 63.8%, 60.0% and 70.0%, respectively, demonstrating a moderate to strong anti-inflammatory effect. Surprisingly, the combination of 0.2% brimonidine (CD07805) with diclofenac (CD08100/02) at 0.1%, 0.3% and 1%, completely reduced TPA-induced ear edema in mice, i.e., by 100%, at all three diclofenac concentrations tested.

TABLE 3

Results of the TPA-induced edema experiment

|  | Ear Edema | | Inhibition vs TPA (%) | Student t-test vs TPA | Student t-test vs CD08100/02 |
|---|---|---|---|---|---|
|  | Mean | sem |  |  |  |
| TPA 0.01% | 16.00 | 1.47 |  |  |  |
| TPA 0.01 + CD153 0.01% | 0.40 | 0.45 | 97.5 | *** |  |
| TPA 0.01% + CD07805 at 0.2% | 8.60 | 2.01 | 46.3 | * |  |
| TPA 0.01% + CD08100/02 at 0.1% | 5.80 | 0.81 | 63.8 | *** |  |
| TPA 0.01% + CD08100/02 at 0.3% | 6.40 | 0.55 | 60.0 | *** |  |
| TPA 0.01% + CD08100/02 at 1% | 4.80 | 2.93 | 70.0 | ** |  |
| TPA 0.01% + CD07805 at 0.2% + CD08100/02 at 0.1% | −0.20 | 0.24 | 101.3 | *** | *** |
| TPA 0.01% + CD07805 at 0.2% + CD08100/02 at 0.3% | −0.20 | 0.24 | 101.3 | *** | *** |
| TPA 0.01% + CD07805 at 0.2% + CD08100/02 at 1% | −0.40 | 0.20 | 102.5 | *** | NS |

The complete anti-inflammatory effect of the combination of brimonidine and diclofenac was comparable with that of 0.01% betametasone valerate (CD0153), which reduced TPA-induced ear edema in mice by 97.5% under the same testing conditions.

These results demonstrate that topical administration of a combination of an α2 adrenergic receptor agonist and a non-steroidal anti-inflammatory agent resulted in improved treatment of an inflammatory skin disorder.

Example 3

Improved Anti-Inflammatory Activity of the Combination of Brimonidine and Diclofenac in Arachidonic Acid-Induced Acute Edema Animal Model The arachidonic acid (AA)-induced acute edema animal model was used to further demonstrate the improved anti-inflammatory effect of brimonidine and diclofenac.

All procedures involving animals were conducted in a fully accredited animal facility and in accordance with the preapproved protocols.

The edema inducer, arachidonic acid, was dissolved in a solution of tetrahydrofuran (THF): methanol (1:1) at 4% by weight to obtain an arachidonic acid solution (AA solution). Test compounds, brimonidine (CD07805) and diclofenac (CD08100/02), were dissolved in the AA solution alone or in combination at desired concentrations. Positive control compound, indomethacin (CD0016), was dissolved in the AA solution at 5% by weight.

Twenty (20) μl of each of the AA solution (negative control), the test compound dissolved in the AA solution, or the positive control dissolved in the AA solution was applied on the internal side of the right ear of the normal, 8-9 week old, female mice (BALB/c ByJ Rj). Different compounds at different dosages were tested on 10 groups of animals, each group having 5 mice (see Table 4).

TABLE 4

Groups of animals used in the AA-induced edema experiment

| Groups: (compounds/dose) | Animal identification |
|---|---|
| Group 1: THF/Methanol | 1 to 5 |
| Group 2: Arachidonic acid 4% | 6 to 10 |
| Group 3: AA + CD0016 at 5% | 11 to 15 |
| Group 4: AA + CD07805 at 0.2% | 16 to 20 |
| Group 5: AA + CD08100/02 at 0.1% | 21 to 25 |
| Group 6: AA + CD08100/02 at 0.3% | 26 to 30 |
| Group 7: AA + CD08100/02 at 1% | 31 to 35 |
| Group 8: AA + CD07805 at 0.2% + CD08100/02 at 0.1% | 36 to 40 |
| Group 9: AA + CD07805 at 0.2% + CD08100/02 at 0.3% | 41 to 45 |
| Group 10: AA + CD07805 at 0.2% + CD08100/02 at 1% | 46 to 50 |

The ear thickness of each of the 50 animals was measured at 0, 1, 2 and 4 hours after the compound application. After the last measurement, the animals were sacrificed by carbon dioxide following a preapproved protocol.

The mean of the ear thickness measured from 5 animals in each of the 10 groups was calculated. The anti-inflammatory activity of a test compound was measured by its ability to reduce AA-induced ear edema, i.e., as the percentage of reduction in ear thickness of animals treated with the test compound and AA as compared with that treated with AA alone.

Figure 2:
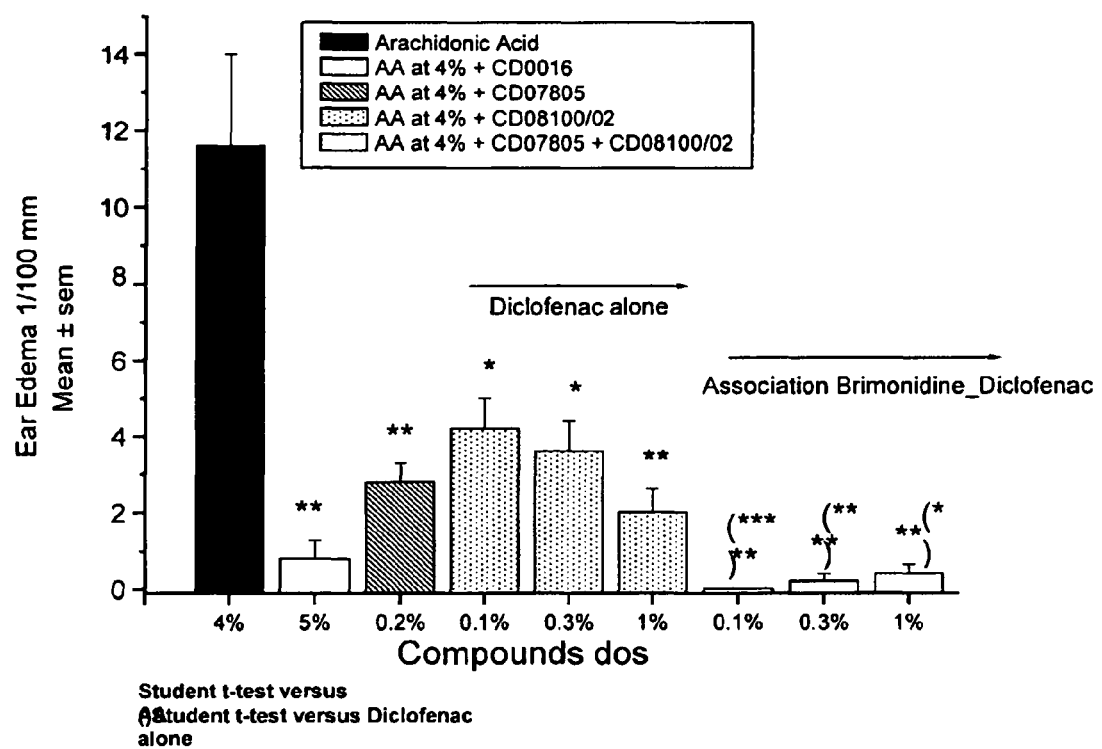
FIG. 2 illustrates the effect of brimonidine and diclofenac, alone or in combination, in reducing the arachidonic acid-induced ear edema in mice: the thickness of the ear was measured 1 hour after the topical administration of the compounds to the ear; the y axis represents the mean ear thickness measured from each group of 5 mice, and the x axis represents the concentration of the compounds.

As shown in Table 5 and FIG. 2, after a single topical application, 0.2% brimonidine (CD07805) alone reduced AA-induced ear edema in mice by up to 80.8%, demonstrating a moderate to strong anti-inflammatory effect. Diclofenac (CD08100/02) alone at 0.1%, 0.3% and 1%, reduced AA-induced ear edema in mice by up to 71.2%, 80.6% and 83.9%, respectively, also demonstrating a moderate to strong anti-inflammatory effect. Surprisingly, the combination of 0.2% brimonidine (CD07805) with diclofenac (CD08100/02) at 0.1%, 0.3% and 1%, completely reduced AA-induced ear edema in mice, i.e., by up to 100%, at all three diclofenac concentrations tested.

The anti-inflammatory effect of the combination of brimonidine and diclofenac was stronger than that of 5% indomethacin (CD0016), which reduced AA-induced ear edema in mice by up to 94.2% under the same testing conditions.

As shown in Table 6, the combination of brimonidine and diclofenac significantly improved the anti-inflammatory effect of diclofenac at all three concentrations tested and all three time measurements.

These results confirmed those obtained from the TPA-induced ear edema study. They further demonstrate that topical administration of a combination of an α2 adrenergic receptor agonist and a non-steroidal anti-inflammatory agent resulted in improved treatment of an inflammatory skin disorder.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

TABLE 5

Results of the AA-induced edema experiment (I)
EAR EDEMA AND INHIBITION vs Arachidonic Acid at 4%

| | 1 h Measurement | | | | 2 h Measurement | | | | 4 h Measurement | | | |
|---|---|---|---|---|---|---|---|---|---|---|---|---|
| | Edema | | Inhibition vs AA | | Edema | | Inhibition vs AA | | Edema | | Inhibition vs AA | |
| Compounds/Doses | Mean | sem | % | t-test | Mean | sem | % | t-test | Mean | sem | % | t-test |
| Arachidonic Acid at 4% | 11.6 | 2.40 | | | 10.4 | 3.57 | | | 6.2 | 2.31 | | |
| AA + CD0016 at 5% | 0.8 | 0.49 | 93.1 | ** | 0.6 | 0.37 | 94.2 | * | 0.4 | 0.24 | 93.5 | * |
| AA + CD07805 at 0.2% | 2.8 | 0.49 | 75.9 | ** | 2 | 0.73 | 80.8 | NS | 1.6 | 0.68 | 74.2 | NS |
| AA + CD08100/02 at 0.1% | 4.2 | 0.80 | 63.8 | * | 3 | 1.24 | 71.2 | NS | 2 | 1.05 | 67.7 | NS |
| AA + CD08100/02 at 0.3% | 3.6 | 0.81 | 69.0 | * | 2.2 | 0.68 | 78.8 | NS | 1.2 | 0.20 | 80.6 | NS |
| AA + CD08100/02 at 1% | 2 | 0.63 | 82.8 | ** | 1 | 0.20 | 90.4 | * | 1 | 0.32 | 83.9 | NS |
| AA + CD07805 at 0.2% + CD08100/02 at 0.1% | 0 | 0.00 | 100.0 | ** | −0.2 | 0.00 | 101.9 | * | 0 | 0.00 | 100.0 | * |
| AA + CD07805 at 0.2% + CD08100/02 at 0.3% | 0.2 | 0.20 | 98.3 | ** | 0.0 | 0.20 | 100.0 | * | 0.4 | 0.40 | 93.5 | * |
| AA + CD07805 at 0.2% + CD08100/02 at 1% | 0.4 | 0.24 | 96.6 | ** | −0.2 | 0.00 | 101.9 | * | 0.2 | 0.20 | 96.8 | * |

TABLE 6

Results of the AA-induced edema experiment (II)
EAR EDMA AND INHIBITION Association vs Diclofenac alone

| | 1 h Measurement | | | | 2 h Measurement | | | | 4 h Measurement | | | |
|---|---|---|---|---|---|---|---|---|---|---|---|---|
| | Edema | | Inhibition vs Diclofenac alone | | Edema | | Inhibition vs Diclofenac alone | | Edema | | Inhibition vs Diclofenac alone | |
| Compounds/Doses | Mean | sem | % | t-test | Mean | sem | % | t-test | Mean | sem | % | t-test |
| Arachidoric Acid at 4% | 11.6 | 2.40 | | | 10.40 | 3.57 | | | 6.2 | 2.31 | | |
| AA + CD07805 at 0.2% | 2.8 | 0.49 | | | 2.00 | 0.73 | | | 1.6 | 0.68 | | |
| AA + CD08100/02 at 0.1% | 4.2 | 0.80 | | | 3.00 | 1.24 | | | 2 | 1.05 | | |
| AA + CD08100/02 at 0.3% | 3.6 | 0.81 | | | 2.20 | 0.68 | | | 1.2 | 0.20 | | |
| AA + CD08100/02 at 1% | 2 | 0.63 | | | 1.00 | 0.20 | | | 1 | 0.32 | | |
| AA + CD07805 at 0.2% + CD08100/02 at 0.1% | 0 | 0.00 | 36.2 | *** | −0.20 | 0.00 | 30.8 | * | 0 | 0.00 | 32.3 | NS |
| AA + CD07805 at 0.2% + CD08100/02 at 0.3% | 0.2 | 0.20 | 29.3 | ** | 0.00 | 0.20 | 21.2 | * | 0.4 | 0.40 | 12.9 | NS |
| AA + CD07805 at 0.2% + CD08100/02 at 1% | 0.4 | 0.24 | 13.8 | * | −0.20 | 0.00 | 11.5 | *** | 0.2 | 0.20 | 12.9 | NS |

The invention claimed is:

1. A method of treating an inflammatory skin disorder or a sign and/or symptom associated therewith in a subject, comprising topically administering to a skin area of the subject a topical composition comprising 0.2% by weight of brimonidine or a pharmaceutically acceptable salt thereof, and 0.1% to 1% by weight of diclofenac or a pharmaceutically acceptable salt thereof, and a pharmaceutically acceptable carrier, wherein the skin area is, or is prone to be, affected by the inflammatory skin disorder or the symptom associated therewith, and the inflammatory skin disorder is rosacea, psoriasis, topic dermatitis, or acne.

2. The method of claim 1, further comprising administering to the subject one or more other treatments and medications for the inflammatory skin disorder or the sign and/or symptom associated therewith.

* * * * *